United States Patent [19]

Weitz et al.

[11] 4,048,165
[45] Sept. 13, 1977

[54] MANUFACTURE OF 1-SUBSTITUTED OXIMINO CYCLO ALKENES-(1)

[75] Inventors: Hans-Martin Weitz, Frankenthal; Kurt Kahr, Neustadt; Rolf Fischer, Heidelberg, all of Germany

[73] Assignee: BASF Aktiengesellschaft, Rheinland-Pfalz, Germany

[21] Appl. No.: 603,440

[22] Filed: Aug. 11, 1975

[51] Int. Cl.$^2$ ........................................... C07D 295/12
[52] U.S. Cl. ............................ 544/166; 260/293.65; 260/326.85; 260/268 R; 548/341; 260/313.1
[58] Field of Search ................... 260/566 A, 247.5 R, 260/293.65, 326.85, 268 R, 309, 309.7, 313.1

[56] References Cited

U.S. PATENT DOCUMENTS

| | | | |
|---|---|---|---|
| 3,293,301 | 12/1966 | Derfer et al. | 260/566 A |
| 3,517,047 | 6/1970 | Ohno et al. | 260/566 A |
| 3,979,455 | 9/1976 | Duranleau et al. | 260/566 A |

FOREIGN PATENT DOCUMENTS 45-9531  4/1970  Japan

*Primary Examiner* — Henry R. Jiles
*Assistant Examiner* — Robert T. Bond
*Attorney, Agent, or Firm* — Keil, Thompson & Shurtleff

[57] ABSTRACT

Manufacture of 1-substituted oximino cycloalkenes-(1) by reacting appropriately substituted cycloalkenes with nitrogen monoxide and oxygen. The products are intermediates in the manufacture of dyes and pesticides.

7 Claims, No Drawings

MANUFACTURE OF 1-SUBSTITUTED OXIMINO CYCLO ALKENES-(1)

This invention relates to a novel process for the manufacture of 1-substituted oximino cycloalkenes-(1) by reacting appropriately substituted cycloalkanes with nitrogen monoxide and oxygen.

It is known to manufacture 1-morpholino-6-oximino-cyclohexene-(1) by reacting 1-morpholino-cyclohexene-(1) with nitrosyl chloride in the presence of triethylamine. More than 12 hours are required to work up the reaction mixture for the purpose of isolating the product therefrom (Tetrahedron Letters, Volume 4, pp. 203 to 206 (1964)). The same compound and the 1-piperidino compound are obtained if, in place of nitrosyl chloride and the base, ethyl nitrite or isoamyl nitrite is used and use is made of $BF_3$-etherate or anhydrous $AlCl_3$ as catalyst. To separate the product, the reaction mixture must be stored for one week in a refrigerator. In the case of the 1-pyrrolidino compound, synthesis only takes place in the absence of solvents and at a cooling bath temperature of $-45°$ C (J. prakt. Chem., Volume 311, pp. 162 to 164 (1969)). A similar synthesis using other alkyl nitrites such as butyl nitrite is described in Japanese Published Application No. 9,531/67, where a reaction time of 10 hours at room temperature is recommended.

All of the above processes require expensive nitrosating agents and a long reaction time or working-up time and unsatisfactory as regards simplicity and economy, particularly for large-scale production.

It is an object of the present invention to provide a novel process for producing 1-substituted oximino cycloalkenes-(1) in a simpler and more economical manner and, in some cases, in better yield and purity and with better space/time yields.

We have found that 1-substituted oximino cycloalkenes-(1) of the formula

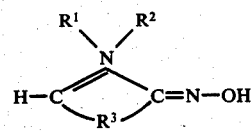

I, in which $R^1$ and $R^2$ are the same or different and individually denote aliphatic radicals or are joined together with the adjacent nitrogen atom to form a heterocyclic ring, and $R^3$ denotes an aliphatic radical, may be prepared in an advantageous manner by reacting cycloalkenes with nitrosating agents provided that cycloalkenes of the formula

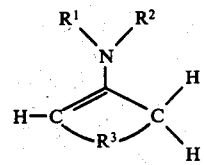

II, where $R^1$, $R^2$ and $R^3$ have the meanings stated above are reacted with from 1 to 2.5 moles of nitrogen monoxide and from 0.25 to 1 mole of oxygen per mole of starting material II in organic solvents which are inert under the conditions of the reaction.

The reaction is represented by the following equation illustrating the use of 1-morpholino cyclohexene-(1):

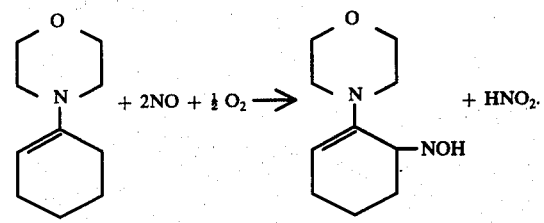

The nitrous acid thus formed reacts in a subsequent reaction with further 1-morpholinocyclohexene-(1), generally in a molar ratio of 1:1, to form nitrosated secondary products.

Compared with the prior art processes, the process of the invention produces 1-substituted oximino cycloalkenes-(1) in a more simple and economical manner and in some cases in better yields and purity and also in better space/time yields. Catalysts are not required. The reaction rate is higher and working-up of the reaction mixture is in some cases shorter and simpler. It is not necessary to effect special measures for cooling the reaction mixture or to work up the reaction mixture for long periods at very low temperatures. All of these advantageous results are surprising in view of the prior art, since it is known that when dinitrogen trioxide is used as nitrosating agent, side reaction occur due to the fact that the initially formed oximes subsequently lead to the formation of pseudonitroles or nitrolic acids (Houben-Weyl, Methoden der organischen Chemie, Volume 10/4, page 22). Houben-Weyl also shows that difficulties are encountered in the accurate metering of gaseous dinitrogen trioxide, such as is also formed in the gas mixture of nitrogen monoxide and oxygen in the process of the invention. Thus the success of the simple procedure of the invention was not to be expected.

Preferred starting materials II and accordingly preferred products I are those in the formulae of which $R^1$ and $R^2$ are the same or different and individually denote alkyl of from 1 to 8 carbon atoms or together with the adjacent nitrogen atom form members of a 5- or 6-membered heterocyclic ring which may contain a further nitrogen atom or an oxygen atom in addition to said adjacent nitrogen atom, and in which $R^3$ is alkylene of from 2 to 10 carbon atoms. The said radicals and rings may be substituted by groups which are inert under the conditions of the reaction, for example alkyl or alkoxy groups each of from 1 to 4 carbon atoms.

Examples of suitable cycloalkenes for using as starting materials II are as follows: 1-morpholinocyclopentene-(1), 1-morpholinocyclohexene-(1), 1-morpholinocycloheptene-(1), 1-morpholinocyclooctene-(1), 1-morpholinocyclononene-(1), 1-morpholinocyclodecene-(1), and 1-morpholinocyclododecene-(1) and the analogous 1-piperidino, 1-pyrrolidino, 1-piperazino, 1-dimethylamino, 1-diethylamino, 1-N-methyl-N-ethylamino, 1-imidazolidino, 1-pyrrolino-(Δ2'), 1-imidazolo, 1-di-n-propylamino, 1-diisobutylamino, 1-dihexylamino, 1-di-t-butylamino, and 1-di-n-butylamino compounds.

The starting material II is reacted with from 1 to 2.5 moles and preferably from 1 to 1.2 moles of nitrogen monoxide and from 0.25 to 1 and preferably from 0.25 to 0.3 mole of oxygen per mole of starting material II. In place of oxygen, use may be made of oxygen-containing gas mixtures, preferably air. The proportions of nitrogen monoxide and oxygen are usually selected so as to correspond to the composition of dinitrogen trioxide. A small excess of nitrogen monoxide has been found to be advantageous. Any substances entrained by the nitrogen monoxide and forming nitrogen monoxide under the conditions of the reaction, for example nitrogen trioxide or nitrogen dioxide, are calculated as nitrogen monoxide and oxygen. A ratio of from 4 to 4.8 moles of nitrogen monoxide to 1 mole of oxygen is preferred.

The reaction is generally carried out at a temperature of from −20° to +100° C and preferably from −10° to +40° C at atmospheric or syuperatmospheric pressure, continuously or batchwise. Examples of suitable solvents are: aromatic hydrocarbons such as toluene, ethylbenzene, o-, m- and p-xylenes, isopropylbenzene and methylnaphthalene; halohydrocarbons, particularly chlorohydrocarbons such as amyl chloride, cyclohexyl chloride, dichloropropane, methylene chloride, dichlorobutane, isopropyl bromide, n-propyl bromide, butyl bromide, chloroform, ethyl iodide, propyl iodide, chloronaphthalene, dichloronaphthalene, carbon tetrachloride, tetrachloroethane, trichloroethane, trichloroethylene, pentachloroethane, o-, m- and p-difluorobenzene, 1,2-dichloroethane, 1,1-dichloroethane, n-propyl chloride, 1,2-cis-dichloroethylene, n-butyl chloride, s-, t- and i-butyl chlorides, chlorobenzene, fluorobenzene, bromobenzene, iodobenzene, o-, p- and m-dichlorobenzenes, o-, p- and m-dibromobenzenes, o-, p- and m-chlorotoluenes, 1,2,4-trichlorobenzene, 1,10-dibromodecane and 1,4-dibromobutane; alkanols and cycloalkanols such as ethanol, n-butanol, isobutanol, t-butanol, cyclohexanol, propanol and methanol; ethers, such as ethyl propylether, methyl-t-butyl ether, n-butyl ethyl ether, di-n-butyl ether, di-iso-amyl ether, diisopropyl ether, anisol, phenetol, cyclohexyl methyl ether, diethyl ether, tetrahydrofuran, thioanisol, $\beta,\beta'$-dichloro diethyl ether; aliphatic or cycloaliphatic hydrocarbons such as heptane, pinane, nonane, o-, m- and p-cymenes, petroleum fractions boiling from 70° to 190° C, cyclohexane, methylcyclohexane, petroleum ether, dekalin, pentane, hexane, ligroin, 2,2,4-trimethylpentane, 2,2,3-trimethylpentane, 2,3,3-trimethylpentane, octane and mixtures thereof. Advantageously, the solvent is used in an amount of from 200 to 10,000% w/w and preferably from 200 to 1,000% w/w, based on starting material II.

The reaction may be carried out as follows:
The air in the apparatus is advantageously first replaced by an inert gas such as nitrogen, whereupon nitrogen monoxide and oxygen are passed into the gas space above the reaction mixture in such a manner that the gases mix just prior to the reaction with the cycloalkene II dissolved in the solvent. The reactor is advantageously provided with a pressure relief valve and it is convenient to carry out the reaction at a pressure slightly in excess of atmospheric, for example a pressure of from 1 to 3 atmospheres gauge. Following the introduction of the gases, preferably over from 1 to 3 hours, the reaction mixture is advantageously maintained at the reaction temperature for a further 0.5 to 1 hour. The product is then separated in conventional manner, for example by filtration, optionally after precipitation, for example by means of water, and optionally followed by recrystallization.

The compounds which may be prepared by the process of the invention are valuable starting materials for the manufacture of dyes and pesticides. Reaction of product I with, say, hydroxylammonium chloride gives the corresponding 1,2-dioximinocycloalkenes. These are agents for binding metal ions, particularly heavy metal ions such as cobalt, copper and, in particular, nickel and are consequently suitable indicators and precipitants for such metals. They are strong chelating agents for magnesium, calcium, aluminum, barium and heavy metal ions including nickel, cobalt, copper, chromium(III), cerium and, in particular, iron(III) ions. They may be used as masking agents for nickel and iron in aqueous solutions and suspensions, where the iron would otherwise be undesirable, for example in the paper and textile industries. In the hydrolysis of product I with weak acids, the heterocyclic or aliphatic amino radical may be replaced by hydroxy groups, for example in the manner described in German Patent Application No. P24 41 349 (O.Z. 30,767). Thus 1-morpholino-6-oximino cyclohexene-(1) is converted to 2-oximino cyclohexanone.

The reaction of products I with nitrosyl halides produces 1,6-dioximino cycloalkanones. Thus 1-piperidino-6-oximinocyclohexene-(1) reacted with nitrosyl chloride produces 2,6-dioximino cyclohexanone in quantitative yield (Japanese Published Application No. 13,653/1972). Such cycloalkanones may serve as starting compounds for the synthesis of amino acids, for example lysine (U.S. Pat. No. 2,999,875). For information on the use thereof, see the art cited.

In the following Examples the parts are by weight unless otherwise stated. The parts by weight relate to the parts by volume as do kilograms to liters.

EXAMPLE 1

33.4 Parts of freshly distilled 1-morpholino cyclohexene-(1) dissolved in 120 parts by volume of distilled n-hexane are placed in a stirred vessel filled with nitrogen and having two separate gas inlets. During 1 hour, 4.9 parts by volume of nitrogen monoxide and 1.1 parts by volume of oxygen are simultaneously passed into the gas space above the solution at 20° C. The apparatus is provided with a relief valve. After the introduction of the gases, the mixture is stirred for a further hour at 20° C. Following the addition of 125 parts of water, the suspension is stirred for 30 minutes at room temperature, whereupon the precipitate is filtered off. After drying, there are obtained 17.9 parts of 1-morpholino-6-oximino-cyclohexene-(1) (42% of theory, based on nitrogen monoxide supplied). m.p. 176° to 177° C (ethanol).

EXAMPLE 2

30.6 Parts of 1-diethylamino cyclohexene-(1) dissolved in 100 parts by volume of cyclohexane are reacted, in the manner described in Example 1, with 4.8 parts by volume of nitrogen monoxide and 1.1 parts by volume of oxygen at 20° C over one hour. After stirring for a further hour, 150 parts of water are added to the mixture which is stirred for a further 30 minutes. The organic phase is separated, washed with water and distilled. There are obtained 14.6 parts of 1-diethylamino-6-oximino cyclohexene-(1) (37% of theory, based on nitrogen monoxide supplied), m.p. 85° C (ethanol).

EXAMPLE 3

33 Parts of 1-piperidino cyclohexene-(1) dissolved in 100 parts by volume of n-hexane are reacted, in a manner similar to that described in Example 1, with 4.9 parts by volume of nitrogen monoxide and 4.7 parts by volume of air over 1 hour at 20° C. After working up as described in Example 1, there are obtained 12.7 parts of 1-piperidino-6-oximino-cyclohexene-(1) (30% of theory, based on nitrogen monoxide supplied), m.p. 170° to 171° C (ethanol).

EXAMPLE 4

50 Parts of 1-morpholino-cyclododecene-(1) dissolved in 120 parts by volume of n-hexane are placed in the vessel. In a manner similar to that described in Example 1, 4.8 parts by volume of nitrogen monoxide and 1.1 parts by volume of oxygen are passed over this solution over 1 hour. Following the introduction of the gases, the resulting precipitate is filtered off. There are obtained 15.9 parts of 1-morpholino-12-oximinocyclododecene-(1) (26.5% of theory, based on nitrogen monoxide supplied), m.p. 146° to 148° (ethanol).

We claim:

1. A process for the manufacture of 1-substituted oximino cycloalkenes-(1) of the formula

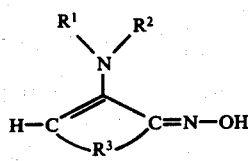

in which $R^1$ and $R^2$ are the same or different and individually denote an alkyl of from 1 to 8 carbon atoms or form, together with the adjacent nitrogen atom, members of a 5- or 6-membered heterocyclic ring selected from the group consisting of morpholino-, piperidino-, pyrrolidino-, piperazino-, imidazolidino-, pyrrolino-(Δ2'), and imidazolo-, and $R^3$ is alkylene of from 2 to 10 carbon atoms, which comprises: reacting cycloalkenes of the formula

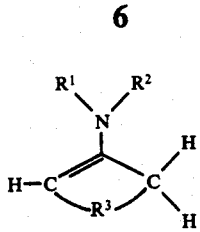

wherein $R^1$, $R^2$ and $R^3$ have the meanings stated above, with from 1 to 2.5 moles of nitrogen monoxide and from 0.25 to 1 mole of oxygen per mole of starting material II in organic solvents which are inert under the conditions of the reaction.

2. A process as set forth in claim 1, wherein the reaction is carried out using from 1 to 1.2 moles of nitrogen monoxide and from 0.25 to 0.3 mole of oxygen per mole of starting material II.

3. A process as set forth in claim 1, wherein the reaction is carried out using a ratio of from 4 to 4.8 moles of nitrogen monoxide to 1 mole of oxygen.

4. A process as set forth in claim 1, wherein the reaction is carried out at a temperature of from −20° to +100° C.

5. A process as set forth in claim 1, wherein the reaction is carried out at a temperature of from −10° to +40° C.

6. A process as set forth in claim 1, wherein the reaction is carried out using as inert solvents aromatic hydrocarbons, halohydrocarbons, alkanols, cycloalkanols, ethers and aliphatic and/or cycloaliphatic hydrocarbons.

7. A process as set forth in claim 1, wherein the reaction is carried out using the solvent in an amount of from 200 to 10,000% w/w, based on starting material II.

* * * * *